US00PP27501P2

(12) United States Plant Patent
Misato

(10) Patent No.: US PP27,501 P2
(45) Date of Patent: Dec. 20, 2016

(54) ***SENECIO* PLANT NAMED 'SUNSENESLISBU'**

(50) Latin Name: *Senecio cruentus*
Varietal Denomination: Sunseneslisbu

(71) Applicant: Tomoya Misato, Shiga (JP)

(72) Inventor: Tomoya Misato, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 144 days.

(21) Appl. No.: 14/544,305

(22) Filed: Dec. 20, 2014

(51) Int. Cl.
*A01H 5/02* (2006.01)

(52) U.S. Cl.
USPC ..... Plt./480

(58) Field of Classification Search
USPC ..... Plt./480
See application file for complete search history.

*Primary Examiner* — Keith Robinson
(74) *Attorney, Agent, or Firm* — C. A. Whealy

(57) ABSTRACT

A new and distinct cultivar of *Senecio* plant named 'Sunseneslisbu', characterized by its upright and uniformly mounded plant habit; freely branching growth habit; freely flowering habit; and daisy-type inflorescences with pale blue-colored ray florets and violet blue-colored disc florets; ray florets with acute or deeply incised apices.

1 Drawing Sheet

Botanical designation: *Senecio cruentus.*
Cultivar denomination: 'SUNSENESLISBU'.

CROSS REFERENCED TO CLOSELY-RELATED APPLICATIONS

Title: *Senecio* Plant Named 'SUNSENESLILAV'
Applicant: Tomoya Misato
Filed: Concurrently with this application
Title: *Senecio* Plant Named 'SUNSENESLIPI'
Applicant: Tomoya Misato
Filed: Concurrently with this application

BACKGROUND OF THE INVENTION

The present invention relates to a new and distinct cultivar of *Senecio* plant, botanically known as *Senecio cruentus*, and hereinafter referred to by the name 'Sunseneslisbu'.

The new *Senecio* plant is a product of a planned breeding program conducted by the Inventor in Higashiomi, Shiga, Japan. The objective of the breeding program is to create new upright and uniformly mounding *Senecio* plants with a freely-branching habit and numerous attractive inflorescences.

The new *Senecio* plant originated from a cross pollination conducted by the Inventor in March, 2008 of a proprietary selection of *Senecio cruentus* identified as code name SNB, not patented, as the female, or seed, parent with a proprietary selection of *Senecio cruentus* identified as code name KPS, not patented, as the male, or pollen, parent. The new *Senecio* plant was discovered and selected by the Inventor as a single flowering plant within the progeny of the stated cross-pollination in a controlled greenhouse environment in Higashiomi, Shiga, Japan in February, 2009.

Asexual reproduction of the new *Senecio* plant by terminal cuttings in a controlled greenhouse environment in Higashiomi, Shiga, Japan since February, 2009 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental, conditions such as temperature and light intensity, without, however, any variance in genotype.

The following traits have been repeatedly observed and are determined to be the unique characteristics of 'Sunseneslisbu'. These characteristics in combination distinguish 'Sunseneslisbu' as a new and distinct *Senecio* plant:

1. Upright and uniformly mounded plant habit.
2. Freely branching growth habit.
3. Freely flowering habit.
4. Daisy-type inflorescences with pale blue-colored ray florets and violet blue-colored disc florets; ray florets with acute or deeply incised apices.

Plants of the new *Senecio* can be compared to plants of the female parent selection. Plants of the new *Senecio* differ from plants of the female parent selection in the following characteristics:

1. Plants of the new *Senecio* and the female parent selection differ in ray floret color as plants of the female parent selection have violet-colored ray florets.
2. Ray florets of plants of the new *Senecio* have acute, or deeply incised apices whereas ray florets of plants of the female parent selection have acute or praemorse apices.

Plants of the new *Senecio* can be compared to plants of the male parent selection. Plants of the new *Senecio* differ from plants of the male parent selection in the following characteristics:

1. Plants of the new *Senecio* and the male parent selection differ in ray floret color as plants of the male parent selection have pink-colored ray florets.

2. Ray florets of plants of the new *Senecio* have acute or deeply incised apices whereas ray florets of plants of the male parent selection have acute or praemorse apices.

Plants of the new *Senecio* can be compared to plants of *Senecio cruentus* 'Sunseneslilav', disclosed in U.S. Plant patent application Ser. No. 14/544,304, and *Senecio cruentus* 'Sunseneslipi', disclosed in U.S. Plant patent application Ser. No. 14/544,303. Plants of the new *Senecio* differ primarily from plants of 'Sunseneslilav' and 'Sunseneslipi' in ray floret color.

Plants of the new *Senecio* can also be compared to plants of *Senecio cruentus* 'Sunsenesubu', disclosed in U.S. Plant Pat. No. 24,461. In side-by-side comparisons conducted in Higashiomi, Shiga, Japan, plants of the new *Senecio* differed from plants of 'Sunsenesubu' in the following characteristics:

1. Plants of the new *Senecio* were more compact and more upright than plants of 'Sunsenesubu'.
2. Plants of the new *Senecio* had smaller and lighter green- colored leaves than plants of 'Sunsenesubu'.
3. Plants of the new *Senecio* flowered four weeks earlier than plants of 'Sunsenesubu'.
4. Plants of the new *Senecio* had smaller inflorescences than plants of 'Sunsenesubu'.
5. Plants of the new *Senecio* and 'Sunsenesubu' differed in ray floret color as plants of 'Sunsenesubu' had violet blue-colored ray florets.
6. Ray florets of plants of the new *Senecio* had acute or deeply incised apices whereas ray florets of plants of 'Sunsenesubu' had acute or praemorse apices.

BRIEF DESCRIPTION OF THE PHOTOGRAPHS

The accompanying photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph at the top of the sheet comprises a side perspective view of a typical flowering plant of 'Sunseneslisbu' grown in a container.

The photograph at the bottom of the sheet is a close-up view of a typical flowering plant of 'Sunseneslisbu'.

DETAILED BOTANICAL DESCRIPTION

The aforementioned photographs, following observations and measurements describe plants grown during the spring in 15-cm containers in an outdoor nursery in Higashiomi, Shiga, Japan and under cultural practices typical of commercial *Senecio* production. During the production of the plants, day temperatures averaged 10° C. and night temperatures averaged 5° C. Measurements and numerical values represent averages for typical flowering plants. Plants were six months old when the photographs and description were taken. In the following description, color references are made to The Royal Horticultural Society Colour Chart, 2007 Edition, except where general terms of ordinary dictionary significance are used.

Botanical classification: *Senecio cruentus* 'Sunseneslisbu'.

Parentage:

*Female, or seed, parent*.—Proprietary selection of *Senecio cruentus* identified as code name SNB, not patented.

*Male, or pollen, parent*.—Proprietary selection of *Senecio cruentus* identified as code name KPS, not patented.

Propagation:

*Type*.—Terminal vegetative cuttings.

*Time to initiate roots, summer and winter*.—About one week at temperatures about 18° C. to 20° C.

*Time to produce a rooted young plant, summer and winter*.—About four weeks at temperatures about 18° C. to 20° C.

*Root description*.—Fine, fibrous.

*Rooting habit*.—Freely branching.

Plant description:

*Plant form and growth habit*.—Upright and uniformly mounded plant habit; daisy-type inflorescences positioned above the foliar plane; freely branching habit; vigorous growth habit.

*Plant height*.—About 25 cm.

*Plant diameter*.—About 22.5 cm.

*Lateral branches*.—Length: About 17.4 cm. Diameter: About 3.4 mm. Internode length:. About 2.5 cm. Strength: Strong. Texture: Slightly pubescent. Color: Close to 144A.

*Leaf description*.—Arrangement: Alternate, simple. Length: About 5.2 cm. Width: About 5.4 cm. Shape: Cordate. Apex: Acute. Base: Cordate. Margin: Shallowly dentate; slightly undulate. Texture, upper surface: Sparsely pubescent. Texture, lower surface: Densely pubescent. Venation pattern: Pinnate; reticulate. Color: Developing leaves, upper surface: Close to 144A. Developing leaves, lower surface: Close to 148C. Fully expanded leaves, upper surface: Close to 146A; venation, close to N144D. Fully expanded leaves, lower surface: Close to 148C; venation, close to 145B. Leaf petioles: Length: About 4.7 cm. Diameter: About 1.8 mm. Texture, upper and lower surfaces: Pubescent. Color, upper and lower surfaces: Close to 144B.

Inflorescence description:

*Appearance*.—Daisy-type inflorescences with narrowly elliptic- shaped ray florets with acute or deeply incised apices; inflorescences arising from upper leaf axils and positioned above the foliar plane; disc and ray florets developing acropetally on a capitulum; inflorescences face upright and outwardly; freely flowering habit with numerous inflorescences developing per plant.

*Fragrance*.—None detected.

*Natural flowering season*.—Plants of the new Senecio begin flowering about 22 weeks after planting; plants flower continuously from winter to late spring in Japan.

*Inflorescence buds*.—Height: About 7.7 mm. Diameter: About 6.2 mm. Shape: Globose. Color: Close to N88B.

*Inflorescence size*.—Diameter: About 4.8 cm. Depth (height): About 1.75 cm. Disc diameter: About 12.1 mm.

*Ray florets*.—Shape: Narrowly elliptic. Length: About 2 cm. Width: About 7.1 mm. Apex: Acute or deeply incised; incisions about 5 mm in length. Base:

Obtuse. Margin: Entire. Aspect: Initially upright, then horizontal and reflexing with development. Texture, upper and lower surfaces: Smooth, glabrous; velvety. Number of ray florets per inflorescence: About 13 in a single whorl. Color: When opening, upper surface: Close to 95B. When opening, lower surface: Close to 94C. Fully opened, upper surface: Close to 100B; color does not change with development. Fully opened, lower surface: Close to 94D; color does not change with development.

*Disc florets*.—Shape: Tubular; apex dentate, five-pointed. Length: About 6.7 mm. Diameter, at apex: About 1.3 mm. Number of disc floret per inflorescence: About 150. Color, immature: Close to N89A. Color, mature: Close to N89B.

*Phyllaries*.—Quantity per inflorescence: About 13 in a single whorl. Length: About 7.5 mm. Width: About 1.7 mm. Shape: Narrowly elliptic. Apex: Acuminate. Base: Fused. Margin: Entire. Texture, upper and lower surfaces: Smooth, glabrous. Color, upper surface: Close to 143A; towards the apex, close to N77A. Color, lower surface: Close to 143B.

*Peduncles*.—Length: About 3.3 cm. Diameter: About 1.5 mm. Strength: Strong. Aspect: Upright to somewhat outwardly. Texture: Smooth, glabrous. Color: Close to 146C.

*Reproductive organs*.—Androecium: Present on disc florets only. Anther shape: Ellipsoidal. Anther color: Close to N89B. Pollen amount: Moderate. Pollen color: Close to 12A. Gynoecium: Present on both ray and disc florets. Stigma shape: Bi-parted. Stigma color: Close to N89B.

*Seeds and fruits*.—Seed and fruit development have not been observed on plants of the new *Senecio*.

Disease & pest resistance: Plants of the new *Senecio* have not been observed to be resistant to pathogens and pests common to *Senecio* plants.

Temperature tolerance: Plants of the new *Senecio* have been observed to tolerate temperatures ranging from about 0° C. to about 30° C.

It is claimed:

1. A new and distinct *Senecio* plant named 'Sunseneslisbu' as illustrated and described.

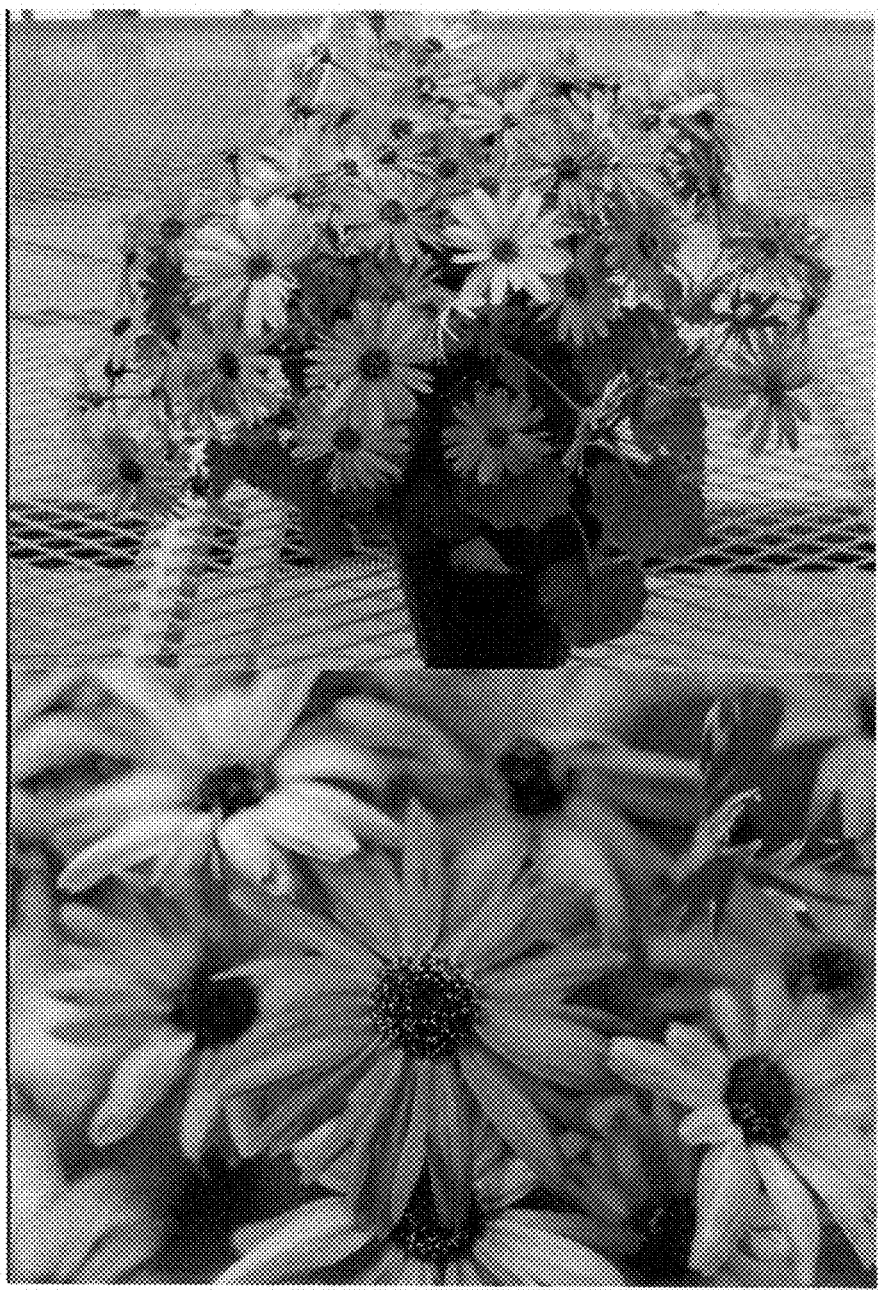

* * * * *